United States Patent [19]

Rea

[11] Patent Number: 5,178,145

[45] Date of Patent: Jan. 12, 1993

[54] SELF RETAINING LARYNGEAL SURFACE ELECTRODE AND METHOD FOR INDEPENDENT IDENTIFICATION OF HUMAN RECURRENT LARYNGEAL NERVE

[76] Inventor: James L. Rea, 2019 Honeysuckle La., Jefferson City, Mo. 65109

[21] Appl. No.: 735,042

[22] Filed: Jul. 24, 1991

[51] Int. Cl.⁵ ............................................. A61B 5/04
[52] U.S. Cl. .................................. 128/642; 128/741
[58] Field of Search ....................... 128/642, 733, 741

[56] References Cited

U.S. PATENT DOCUMENTS 4,155,353   5/1979   Rea et al. .................. 128/733 X
5,024,228   6/1991   Goldstone et al. ......... 128/733 X

OTHER PUBLICATIONS

Payne et al., "Surface Electrode for Laryngeal Electromyography" *J. Neurology, Neurosurgery, and Psychiatry*, 43:853-860, 1980.

Payne, J. et al., "Respiratory Activity of the Vocal Cords in Normal Subjects and Patients with Airflow Obstruction; an Electromyographic Study", *Clinical Science*, 61:163-167, 1981.

Fujita, M. et al. "A New Surface Electrode for Recording from the Posterior Cricoarytenoid Muscle", *Laryngoscope*, 99:316-320 Mar. 1989.

Silverstein, H. et al. "Intraoperative Facial Nerve Monitoring", *Otolaryngologic Clinics of North America*, vol. 24, No. 3, Jun. 1991.

*Primary Examiner*—Lee S. Cohen
*Assistant Examiner*—Samuel Gilbert

[57] ABSTRACT

An electrode for laryngeal electromyography comprises a curved planar insulator formed by an insulating conformational plate covered with insulating polyethylene foam tape with three conductive surface electrode plates mounted in a spaced apart relation such that two surface electrode plates are on the anterior aspect and one on the posterior aspect. Three flexible electrical wires have one end connected to the conductive electrode plates, and the other end adapted for connection to an electrical signal monitor. A steering tab projects outwardly of the conformational plate and is shaped for inclusion with the twisted electrical wires in a tube of heat shrink type electrical insulator material to provide a handle for manual insertion. The two anterior surface electrode plates are of a width and height to cover the human posterior cricoarytenoid muscle and the insulating conformational plate is of a width and height to allow positioning and retention within the human laryngopharynx in the postcricoid space adjacent the posterior cricoarytenoid muscle of the larynx. The single posterior surface electrode plate is positioned in the posterior laryngopharynx facing the spinal column. A signal generating probe is applied to surgically exposed internal tissue in the area surrounding the recurrent laryngeal nerve, whereby contact between the probe and the laryngeal nerve excites the posterior cricoarytenoid muscle and the monitor, thereby indicating to the surgeon the exact location of the nerve.

6 Claims, 4 Drawing Sheets

Fig. 4-A
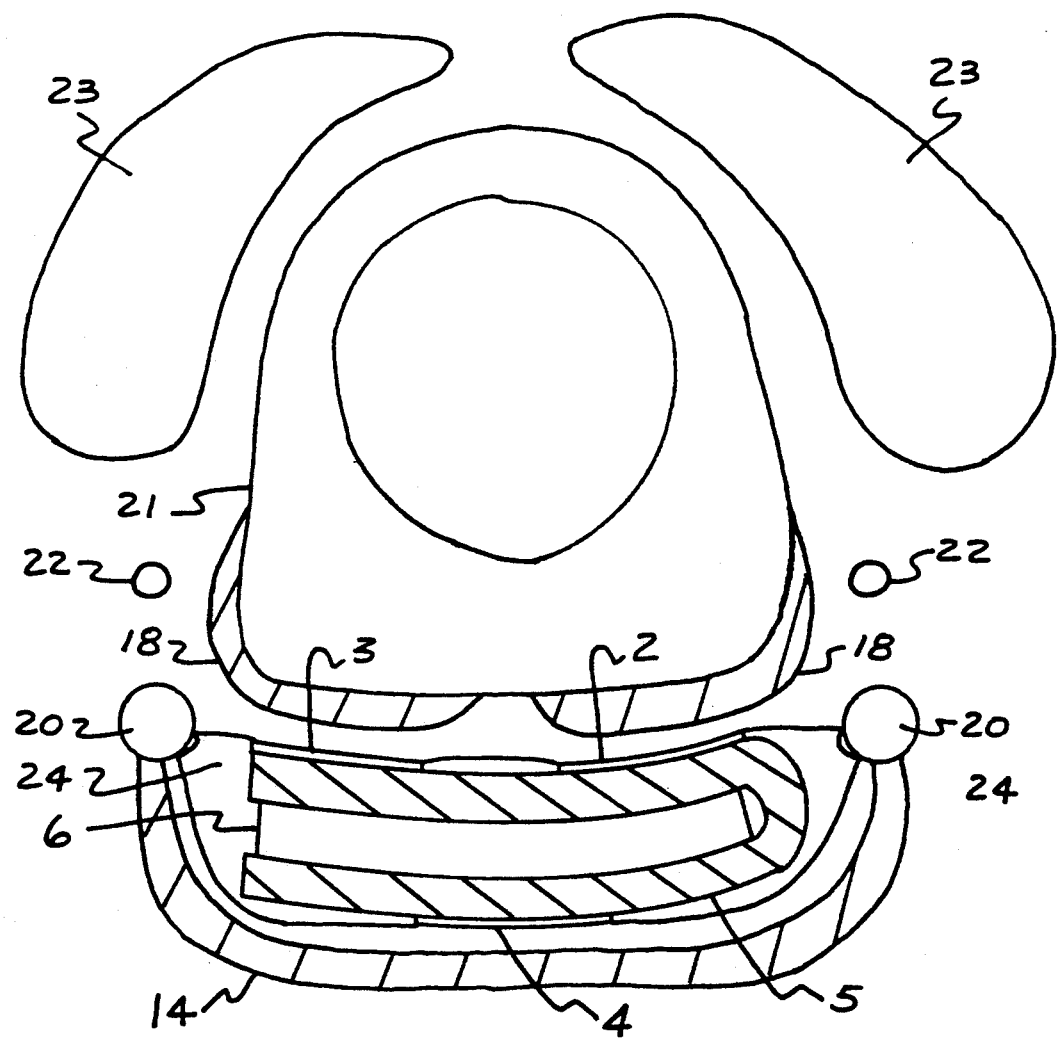
Fig. 4-B
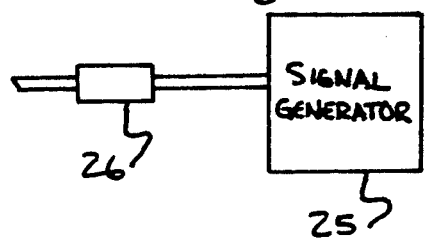

SELF RETAINING LARYNGEAL SURFACE ELECTRODE AND METHOD FOR INDEPENDENT IDENTIFICATION OF HUMAN RECURRENT LARYNGEAL NERVE

BACKGROUND OF THE INVENTION

This invention relates to electrodes, and in particular to an electrode and method for locating the recurrent laryngeal nerve in a surgery patient.

A quite serious and recurring problem for otolaryngologists is the post operative side effect of vocal cord paralysis following thyroid surgery. Even the best and most experienced surgeons, using the most sophisticated equipment heretofore available, encounter a substantial hazard that the recurrent laryngeal nerve will be severed, stretched or bruised during surgery on or about the thyroid gland. This surgical hazard is a result of several factors, including the fact that the recurrent laryngeal nerve lies just posterior to the most inferior portion of the thyroid gland, and is very small and delicate. Further, it is quite difficult to distinguish this nerve from the background tissue when the area about the thyroid gland is inflamed, as well as covered with blood following the initial incision. As the result of these aforementioned complications, the risk of vocal cord damage following thyroid surgery is very high, and also is quite serious in that it can result in the patient's complete loss of speech. Even if the laryngeal nerve has simply been stretched or bruised, the loss of speech may last for several months. In the unfortunate cases where the nerve is completely severed, the paralysis is permanent, and surgical attempts to repair the same have not yet proven successful.

Attempts to identify the recurrent laryngeal nerve by monitoring the human laryngeal musculature (voice box) by electromyography with indwelling needle electrodes have been successful but additional risk from this procedure has been discovered. The puncture of the laryngeal musculature with needle electrodes invariably causes some bleeding in the muscle. The risk of muscle damage from scarring, risk of possible abscess formation and the trauma of invasive needle monitoring itself has made this method impractical and useless as a routine clinical technique.

SUMMARY OF THE INVENTION

The principal objects of the present invention are: to provide an electrode and method for laryngeal electromyography to locate a recurrent laryngeal nerve; to provide such an electrode and method for continuous, intraoperative laryngeal nerve location during thyroid surgery; to provide such an electrode and method which is easily inserted in the patient and adapted for reliable operation; to provide such an electrode and method which is simple and accurate in operation whereby surgeons without extensive experience in thyroid surgery may conduct said surgery, yet avoid damage to the laryngeal nerve; to provide such an electrode having a configuration to conform to the human posterior laryngeal space (laryngopharynx) preventing inadvertent removal of the electrode from the area of patient's laryngeal musculature; to provide such an electrode and method to allow monitoring of the posterior circoarytenoid muscle of the larynx, a muscle innervated by the recurrent laryngeal nerve, without resort to needle invasion of other laryngeal musculature; to provide such an electrode and method including an audio monitor, whereby the location of the recurrent laryngeal nerve may be determined while the surgeon maintains continuous sight observation of the area of surgery; to provide such an electrode and method which allows insertion of the electrode into the postcricoid space without need for violation of the laryngeal musculature with other invasive retention qualities; to provide such an electrode and method for accurately and securely placing the electrode through the pharynx (throat) into the patient's postcricoid space without interfering with other equipment; and to provide such and electrode which is economical to manufacture, efficient in use, and particularly well adapted for the proposed use.

Other objects and advantages of this invention will become apparent from the following description taken in connection with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4-A is an enlarged, partially schematic, end view of the electrode and adjacent portions of the postcricoid laryngopharynx; the plane of view as defined in FIG. 3.

FIG. 4-B is a representation of the signal generator.

DETAILED DESCRIPTION OF THE PREFERRED EMBODIMENTS

Figure 1:
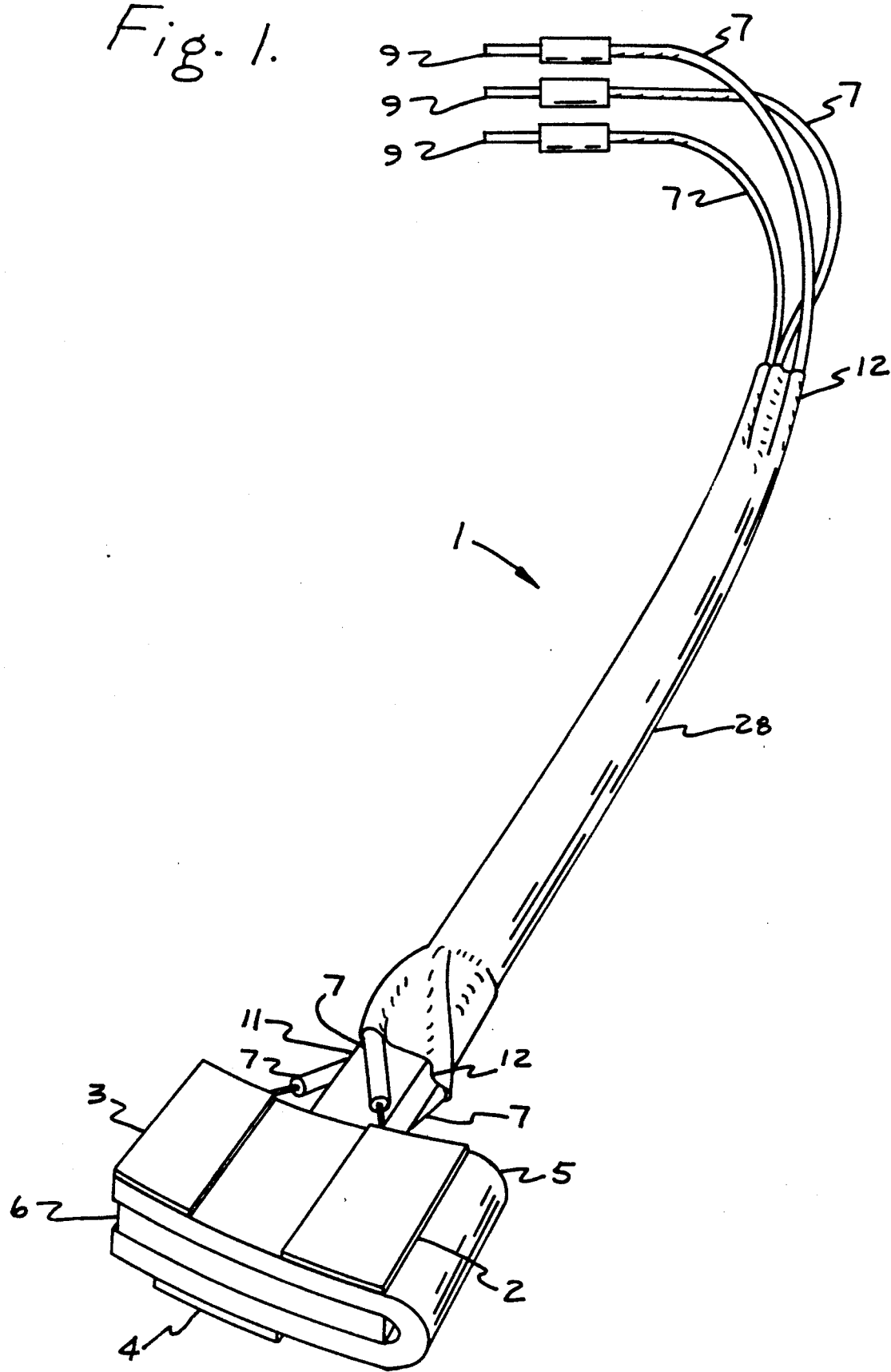
FIG. 1 is a perspective view of an electrode embodying the present invention.

Referring more in detail to the drawings:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and is a representative basis for teaching one skilled in the art to variously employ the present invention and virtually any appropriately detailed structure.

The reference numeral 1 generally designates an electrode embodying the present invention and comprising an electrical conductor surface electrode plate 2, 3, and 4 mounted in a spaced apart relation therein attached to insulating tape 5 which is further attached to an insulating conformational plate 6. Three flexible electrical conductors or wires 7 have one end 8 attached to a surface electrode plate 2, 3, or 4 respectively, and the other end 9 adapted for connection to an electrical signal receiver and monitor. An insulating coating 12 encases the wires 7 and a steering tab 11 projection from the rigid conformational plate 6 to form an insertion handle 28.

For purposes of this description, length will generally parallel the axial dimension of the insertion handle 28 and width will be substantially perpendicular to length and in the long dimension of the rigid conformational plate 6, top and bottom will be established as in the view in FIG. 1, superior will be in the direction of the monitor attachment wires 9, and inferior will be in the direction surface plate electrodes of electrode 1. The surface electrode plate 2, 3, and 4 is constructed of a metallic conductive layer of silver ink, flexograph silver deposition, or similar electrically conductive medium. Surface electrode plate 2 is for monitoring the patient's left posterior cricoarytenoid muscle and is approximately 12.5 mm in width and 15.0 mm in length. Surface electrode plate 3 is nearly 9.38 mm in width and 15.0 mm in length and for monitoring toward the patient's right side. Surface electrode plate 4 is about 12.5 mm in width and 15.0 mm in length and is positioned greater than 5.0 mm from the left edge of the electrode. Surface electrode plate 2, 3, and 4 are attached with conductive adhesive of the silver loaded conductive adhesive or other type to electrical wires 7 and by nonconductive acrylic resin or other type to the polyethylene tape layer 5.

The conformational plate 6 is constructed of 1/16 inch or similar medical grade high density polyethylene and has a concave curvature toward the larynx of nearly 6 cm radius and has two holes 8 of diameter in the nature of 0.8 cm positioned centrally on the left and right side of the plate. The rigid conformational plate 6 at its superior aspect has a steering tab 11 which is planar to the conformational plate, extends about 2 cm into the cylindrical tube of the nature of 4 mm in width and of a substantially rectangular configuration.

Medical grade foam polyethylene tape of the nature of 1/32 inch thickness 5 is attached to the rigid conformational plate 6 by nonconductive adhesive of an appropriate type which adheres to plate 6 and additionally adheres through holes 8 to itself. Plate 6 is convex toward the top surface with a radius approaching 6.0 cm. The dimensions of the polyethylene foam tape layer 5 in the nature of 15 mm height and 60 mm width. The rigid conformational plate 6, and relative positions of the electrical surface electrode plates 2, 3, and 4 provide for the positioning of the electrode in the postcricoid area of the laryngopharynx of the human patient with electrical surface electrode plate 2 positioned under the left posterior cricoarytenoid muscle and with electrical conductor plate 3 positioned under the right posterior circoarytenoid muscle. The electrical conductor plate 4 is positioned posteriorly facing the posterior laryngopharynx at the inferior constrictor muscle and in substantially opposite facing relationship to electrical surface electrode plates 2 and 3. This relationship between the paired electrical surface electrode plates 2 and 3 and the opposite facing single surface electrode conducting plate 4 allows for the optimal monitoring of electromyographic signals where the paired plates 2 and 3 will be the "positive" inputs and the plate 4 will be the "negative" input. In a differential amplification type monitoring device which is commonly used for electromyographic monitoring, the negative input plate should be placed between the two positive plates but separated by insulator from the target muscle monitored by the positive plates in order to maximize signal of interest and minimize spurious electromagnetic signals. Electrode 1 fulfills this condition thereby optimizing the signal reception from the posterior cricoarytenoid muscles of the respective side of the larynx.

The flexible electrical conductors or wires 7 include a conductor core of metallic type and an insulative sheath or coating molded or otherwise axially fixed thereabout. The lower terminal end of each wire 7 is associated with each electrical surface electrode plate 2, 3, and 4 in a conductive manner with silver loaded conductive adhesive with the insulative sheath minimally stripped to allow the contact. The conductors are very fine in the nature of 40 gauge and length 6 inches to facilitate threading the same into the patient's laryngopharynx. The wires are twisted about each other to alleviate the effect of spurious electromagnetic fields which might impinge thereon, and otherwise effect the received signal at the monitor 10.

The flexible electrical conductors or wires provide the input of electrical signals from plates 2 and 3 to the "positive" aspect of an electromyographic monitor instrument with plate 4 serving as a reference ground, identified as the "negative" aspect of input to an electromyographic monitor instrument 10. The flexible electrical conductors 7 leave the electrode body at its superior aspect 8, are twisted to reduce random electrical activity and travel substantially parallel to the rigid steering tab 11. A sheath of tubing 12 of the heat shrink type of about ¼ in diameter and 5 inches length is encased over the flexible electrical conductors 7 and rigid steering tab 11 and heat treated or otherwise shrunk to firmly axially fix these structures. The encased combination of flexible electrical conductors 7, rigid steering tab 11, and tubing 12 provides a cylindrical manual handle 28 for remotely manipulating the electrode body in insertion deep into the patient's laryngopharynx. This assists the user in quickly and accurately placing the electrode into the postcricoid laryngopharynx and in also quickly and safely removing the electrode from the patient at the termination of the monitoring episode.

Figure 2:
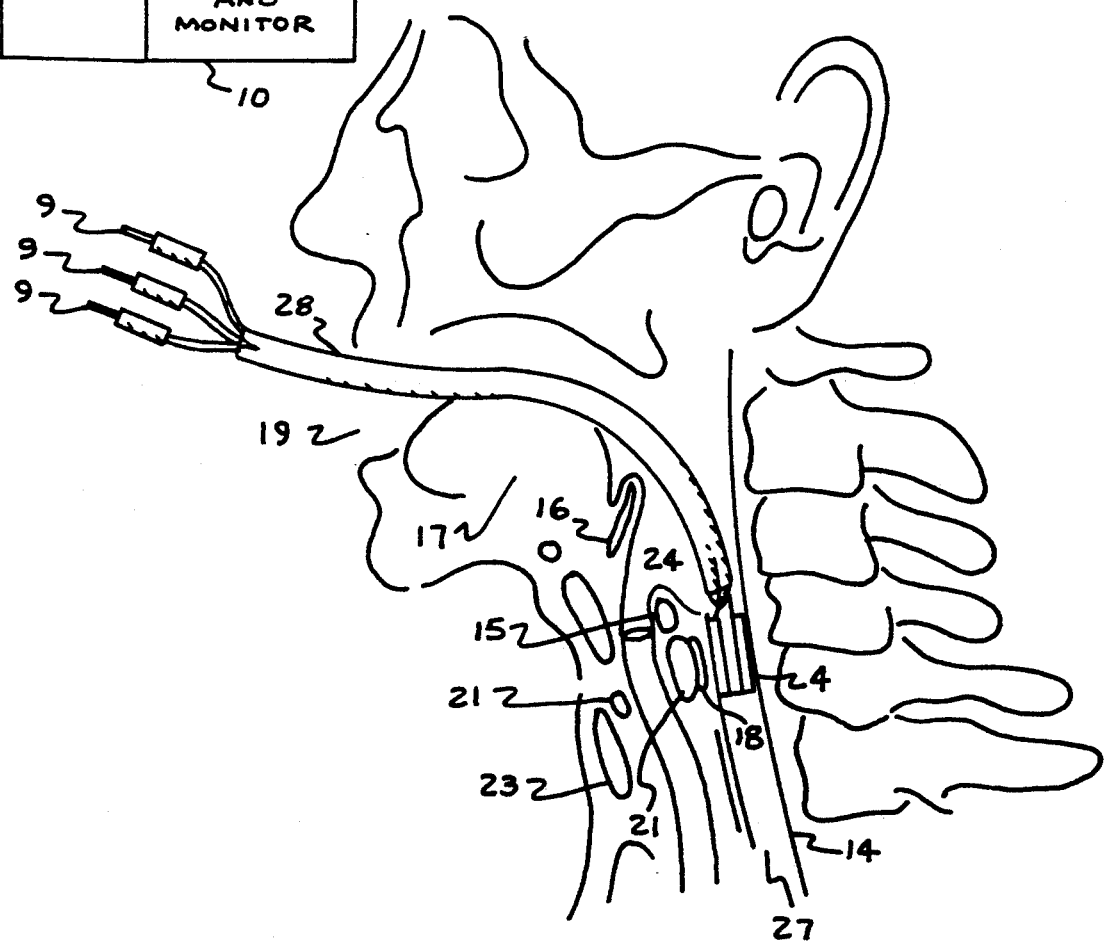
FIG. 2-A is a partially schematic view of a sagittal section of a patient, the electrode positioned therein at the postcricoid area of the laryngopharynx, and shown in section, and illustrates a method for laryngeal electromyography embodying the present invention.

The electrode 1 is particularly adapted for use in conjunction with a method for locating the recurrent laryngeal nerve in a thyroid surgery patient. The patient is first anesthetized, which typically includes the insertion of an intratracheal tube into the patient's mouth and into his trachea. The person who is to insert the electrode 1, such as the anesthesiologist, surgeon, or the like, then grasps the cylindrical manual handle and inserts the electrode body into the mouth of the patient with the concave surface facing upward. A laryngoscope, a lighted device for exposing and examining the larynx, is similarly placed into the patient, such that the person inserting the electrode may accurately position the same. For purposes of description herein, the terms "anterior and posterior" will refer to the anatomy of the patient and the terms will refer herein, respectively to the concave or top and convex or bottom sides of the electrode as oriented in FIG. 1. The laryngoscope is used to raise the larynx and the endotracheal tube so as to expose the posterior laryngopharynx 24 to view and the body of the electrode is positioned as illustrated in FIG. 2, distal, or toward the patient's feet, into the laryngopharynx and posterior to the arytenoid cartilages 15 and cricoid cartilage 21 and apposed to the posterior cricoarytenoid muscles 18. The electrode body is of a configuration that in the average sized adult human when it is placed posterior to the larynx in the midline and when the larynx is gently set down on the electrode, only the most proximal (toward the mouth)

aspect of the electrode with the lower end 8 of each flexible electrical conductor will continue to be in view. This description of the electrode is understood to include possible variations in size of the electrode to accommodate patients of various ages, sizes, and anatomic configurations. The electrode is generally of sufficient size that it cannot be placed further into the esophagus 27 without excessive pressure. The laryngoscope is then gently removed without displacing the electrode.

The upper ends of each of the wires 7 are connected via adapter 9 with the signal receiver and monitor 10 which is positioned at a convenient location adjacent the surgery site. The signal receiver and monitor comprises a device which will receive an electrical signal originating in the posterior cricoarytenoid muscle 18 and transmitted thereto through the wires 7, and provide a display of the signal. The signal receiver and monitor may comprise an oscilloscope or the like, and is preferably a mechanism which provides an audible alarm upon receipt of the electrical signal, whereby the location of the recurrent laryngeal nerve can be determined while the surgeon maintains continuous sight observation of the area of surgery.

Figure 3:
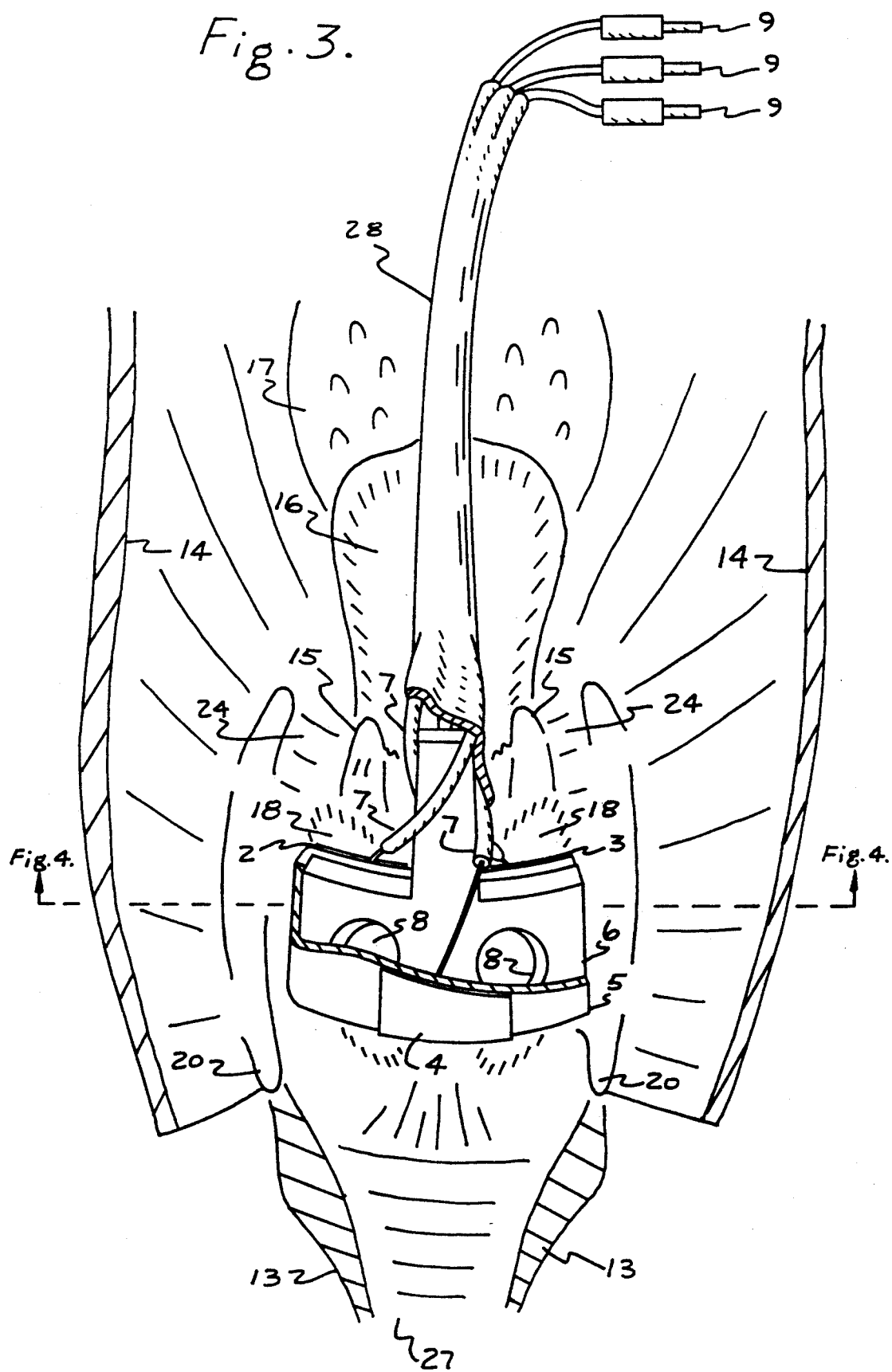
FIG. 3 is a full scale, cut away view of the human patient laryngopharynx showing the electrode in position at the postcricoid area with a portion broken away to reveal internal construction.

The postcricoid larynx is a space best illustrated in FIG. 3 which is a partially schematic, open posterior view of the laryngopharynx with a cutaway electrode shown in place opposite the posterior cricoarytenoid muscle 18. Further displacement of the electrode body into the esophagus 27 is seen to be prevented by relative funnel configuration and tight muscle sphincter 13 at the upper esophagus 27. The parallel opposing firm cartilaginous structures of the larynx known as the inferior cornu 20 are seen to limit the lateral movement of the electrode body by their rigid barrier and by the attached inferior constrictor muscles 14. The posterior circoarytenoid muscles are seen in faint relief at the posterior cricoid face and apposing respectively surface conductive plate 2 on the left and 3 on the right. The surface conductive plate 4 faces the posterior constrictor muscle where the two sides meet in the posterior midline. The cylindrical tube 12 passes proximal, toward the mouth, between the arytenoid cartilages 15, posterior to the epiglottic cartilage 16 and posterior to the tongue 17 before exiting at the mouth 19. The weight of the larynx anteriorly, the friction of the soft tissue posteriorly 14, the relative square sides of the electrode 1, the confirmation between the convex anterior face of the electrode 1 and the cricoid cartilage and the attached posterior cirioarytenoid muscles, the lateral restriction of the inferior cornu 20, and securing of the cylindrical tube 12 at the mouth, all prevent the electrode body from displacing out of position.

FIG. 4 is a cutaway through the level of the cricoid cartilage as demonstrated in FIG. 3 and facing toward the mouth of the patient with electrode 1 positioned in the postcricoid laryngopharynx 24. The close approximation of the anterior facing conductive surface electrode plates 2, and 3 to the posterior cricoarytenoid muscles 18 is seen. The posterior facing of the conductive surface electrode plate 4 toward the inferior constrictor muscle 14 is readily apparent. The particular adaptation of the curvature of the rigid conformational plate to the posterior aspect of the cricoid cartilage 21 is also apparent. Anterior to the cricoid cartilage the thyroid gland 23 is seen in partial schematic. Just posterior to the thyroid gland 23 is seen the anterior branch of the recurrent laryngeal nerve 22.

A signal generator 25 includes a probe 26 and provides means for applying an electrical signal to the recurrent laryngeal nerve 22. The signal is of a relatively low voltage, in the nature of five volts, and is preferably a repetitive stimuli of low frequency, short pulses, in the nature of 4 pulses per second stimulation rate.

After the surgeon has made his initial incision, and is approaching the area of the recurrent laryngeal nerve 22, he simply applies the probe 31 to the area in which he believes the nerve to be located. If the probe contacts the laryngeal nerve, the signal applied thereto by the signal generator 25 is transmitted through the laryngeal nerve to the posterior cricoarytenoid muscle which in turn is thereby excited. Excitement of the posterior cricoarytenoid muscle 18 causes an electrical impulse to be generated therein and is transmitted through the electrical conductive plates 2, or 3 and the wires 7 to the signal receiver and monitor 10. The electrical conductive plate 4 serves as an electrical ground for the signal receiver and monitor. In the case of an audio monitor, the device shall emit popping sounds in a frequency which corresponds to the recognized warning tone emitted by signal receiver and monitor. The surgeon need only recognize the characteristic frequency of these popping sounds to know that he has located the recurrent laryngeal nerve. After having determined the location of the nerve, the surgeon can work very slowly and carefully in this area so as to insure the nerve is not injured. The electrode 1 may be removed from the patient by simply pulling on the wires 7 and threading the same back distally through the patient's mouth.

It is to be understood that while we have illustrated and described certain form of our invention, it is not to be limited to the specific forms or arrangements herein described and shown.

We claim:

1. An electrode for laryngeal electromyography comprising:
   a) a rigid electrical insulator having an anterior and a posterior aspect; the anterior aspect being somewhat concave and the posterior correspondingly convex specifically for inserting and retaining in the human laryngopharynx opposite the posterior cricoarytenoid muscle;
   b) a pair of electrical conductive plates, mounted on said insulator said conductive plates facing anterior in a mutually spaced apart relation, and thereof for facing the posterior aspect of a human larynx at the level of the posterior cricoarytenoid muscle;
   c) a surface conductive plate for electrical reference ground, mounted on said insulator posterior aspect; said surface conductive plate facing posterior, and thereof for facing the posterior laryngopharynx at the larynx level.

2. An electrode as set forth in claim 1 wherein:
   a) said electrical insulator has a width substantially equivalent to the width of the separate human posterior cricoarytenoid muscles as attached to the posterior aspect of the human cricoid cartilage.

3. An electrode as set forth in claim 1 wherein:
   a) said electrical insulator has a length substantially equivalent to the length of the posterior human larynx at the level of the posterior cricoarytenoid muscle.

4. An electrode as set forth in claim 1 wherein:
   a) said electrical conductive plates constituted for inserting and retaining in the human posterior laryngopharynx for purposed of continuous collection of electrical signals from the human posterior cricoarytenoid muscle and adapted for purpose of connection to a signal monitor.

5. A method for locating a recurrent laryngeal nerve in a surgery patient comprising the steps of:
   (a) providing a laryngeal electrode having electrically conductive plates mounted on an insulator, a curved anterior face to match the anatomy of the posterior human larynx at the level of the posterior circoarytenoid muscle, two anterior surface conductive plates and one posterior plate allowing sampling individually of the right and left posterior circoarytenoid muscles anteriorly each electrically conductive plate having a flexible electric conductor connected therewith; and providing for a posterior electrical reference; and a height and width which promotes insertion and retention into the postcricoid laryngopharynx;
   (b) guiding said electrode by direct laryngoscopy through a pharynx portion of said patient into the postcricoid laryngopharynx portion thereof;
   (c) retaining of said electrode in the postcricoid laryngopharynx for the duration of surgery to allow monitoring of the posterior cricoarytenoid muscle;
   (d) connecting each of the flexible electrical conductors with a monitor for sensing impulses in said individual posterior cricoarytenoid muscle;
   (e) providing a probe for exciting internal tissue in and surrounding the laryngeal nerve and applying said probe thereto, whereby exciting of same side posterior cricoarytenoid muscle is sensed by a surface electrode and said monitor thereby indicating the exact location of said nerve.

6. A method as set forth in claim 5 wherein:
   (a) said monitor provides an audible alarm whereby the location of said nerve is determined while maintaining continuous sight observation of said area of surgery.

* * * * *